United States Patent
Sun

(10) Patent No.: US 8,765,836 B2
(45) Date of Patent: Jul. 1, 2014

(54) HYBRID POLYMER NETWORK COMPOSITIONS FOR USE IN DENTAL APPLICATIONS

(75) Inventor: Benjamin J. Sun, York, PA (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/657,691

(22) Filed: Jan. 26, 2010

(65) Prior Publication Data

US 2012/0157566 A1   Jun. 21, 2012

Related U.S. Application Data

(60) Provisional application No. 61/206,060, filed on Jan. 27, 2009.

(51) Int. Cl.
*A61K 6/083* (2006.01)
*A61C 13/087* (2006.01)

(52) U.S. Cl.
USPC .................. 523/117; 523/115; 433/228.1

(58) Field of Classification Search
CPC ... A61K 6/083; A61C 13/087; A61C 2013/00
USPC ................ 523/117, 115; 433/222.1
See application file for complete search history.

(56) References Cited

U.S. PATENT DOCUMENTS

| | | | |
|---|---|---|---|
| 3,218,711 A | 11/1965 | Connan | |
| 3,632,677 A | 1/1972 | Petner et al. | |
| 3,755,898 A | 9/1973 | Warren | |
| 4,067,853 A | 1/1978 | Schmitt et al. | |
| 4,396,377 A | 8/1983 | Roemer et al. | |
| 4,396,476 A | 8/1983 | Roemer et al. | |
| 4,445,863 A | 5/1984 | Lang et al. | |
| 4,551,486 A | 11/1985 | Tateosian et al. | |
| 4,698,373 A | 10/1987 | Tateosian et al. | |
| 4,711,913 A | 12/1987 | Tateosian et al. | |
| 4,863,977 A | 9/1989 | Tateosian et al. | |
| 4,970,032 A | 11/1990 | Rotsaert | |
| 5,151,044 A | 9/1992 | Rotsaert | |
| 5,210,109 A | 5/1993 | Tateosian et al. | |
| 5,452,219 A | 9/1995 | Dehoff et al. | |
| 5,691,905 A | 11/1997 | Dehoff et al. | |
| 5,908,299 A | 6/1999 | Dehoff et al. | |
| 6,063,830 A | 5/2000 | Deguchi et al. | |
| 6,174,168 B1 | 1/2001 | Dehoff et al. | |
| 6,196,843 B1 * | 3/2001 | Kawaguchi et al. | 433/212.1 |
| 6,384,107 B2 | 5/2002 | Liu | |
| 6,488,503 B1 | 12/2002 | Lichkus et al. | |
| 7,189,076 B1 | 3/2007 | Rosenfeld | |
| 7,368,486 B2 | 5/2008 | Erdrich | |
| 2012/0157566 A1 | 6/2012 | Sun | |

FOREIGN PATENT DOCUMENTS

| | | |
|---|---|---|
| EP | 0677286 B1 | 8/1988 |
| EP | 1264581 B1 | 7/2006 |
| WO | 2008062938 A1 | 5/2008 |

OTHER PUBLICATIONS

International search report, application 2010000207, published Jan. 26, 2010.
International written opinion, application 2010000207, published Jan. 26, 2010.

* cited by examiner

*Primary Examiner* — Tae H Yoon
(74) *Attorney, Agent, or Firm* — David A. Zdurne; Douglas J. Hura; Leana Levin

(57) ABSTRACT

A dental appliance comprising a hard, shaped body having at least one portion comprising a polymerized blend of: From 0% to about 50% of an uncrosslinked polymer capable of dissolving in component; From about 0% to 50% of a monofunctional polymerizable monomer; From about 0% to 40% of a highly crosslinked polymer in the form of ground particles having average diameters up to about 500 microns; From about 0% to 50% of a crosslinked polymer in the form of discrete particles having average diameters up to about 500 microns and being easily swellable by said monomer; and From about 5% to about 35% of a di- or polyfunctional crosslinking agent.

18 Claims, No Drawings

HYBRID POLYMER NETWORK COMPOSITIONS FOR USE IN DENTAL APPLICATIONS

BACKGROUND OF THE INVENTION

This invention provides hybrid polymerizable compositions useful for a wide range of applications. The compositions are particularly useful in the dental field, where such compositions can be used in the formation and construction of artificial teeth, enamel layers, denture bases, denture baseplates, denture liners, denture repair, splints, orthodontic appliances, custom trays, veneers, crowns and bridges, repairs for natural teeth, restorations, fillings, and the like. More specifically, the invention relates to polymeric compositions comprising cross-linked polymers, ground highly cross-linked polymers, monomers, and multifunctional crosslinking monomers or oligomers for said monomers, and optionally uncross-linked polymers which form precursor blends. These precursor blends are capable of being formed or molded and polymerized to provide articles possessing superior wear resistance, physical and physiochemical properties. Furthermore, the compositions have excellent molding properties and processing capabilities useful in the production of artificial teeth, dental crowns, or other dental restorations. This invention also includes the artificial teeth and other restorations produced from such materials.

Artificial teeth should exhibit certain desirable physical characteristics to be suitable for use and offer desirable benefits to patients. For example, they should be hard for effective chewing and resistant to abrasion and chipping during use. They also should be durable and stable to solvents, foods, water, cold and hot and maintain esthetics without discoloration. In addition, they should have good esthetics to mimic natural dentition with esthetically acceptable color, i.e., close to that of natural teeth. The teeth should not cause excessive wear to opposing natural or artificial teeth, crowns or bridges, should not wear or deform out of occlusion, and should be capable of being bonded firmly to supportive structures. They should also be adjustable to ordinary means of physical shaping, grinding, and polishing.

Typically, artificial denture teeth are either methacrylate-based plastic teeth or ceramics-based porcelain teeth. In general, artificial plastic teeth are made from PMMA and modified PMMA polymers and MMA and modified MMA liquids. Some composite based teeth are also available in the market. Recently, plastic teeth have largely eliminated porcelain teeth from the denture tooth market due to various advantages, such as better bond to the denture base, lighter weight, toughness, less undesirable noises during chewing, and less wear, to the opposing natural or artificial teeth, crown, or bridge. However, plastic teeth have the disadvantage of being more subject to wear than porcelain teeth. Of the presently available organic compositions used for the construction of artificial teeth, most are composed of acrylics, often cross-linked by polyfunctional moieties. While such compositions are commonly used for artificial teeth, they nonetheless possess certain drawbacks. In general, artificial teeth made of currently available acrylic compositions do not have sufficient wear resistance and can be deformed by relatively low biting forces. The deficiency in wear resistance and limited loading capability of current polymeric artificial teeth are apparent when they are compared to natural or ceramic teeth, crowns or bridges. In addition, the use of implant therapy and over dentures becomes more popular, where highly wear resistant artificial teeth are imperative. Thus, there is a need for artificial teeth having better wear resistance, durability and load-bearing capability.

The patent literature disclose various dental compositions made with higher cross-linked polymers and prepolymers, and composites incorporated with inorganic particles in the polymer matrix.

For example, Erdrich et al., U.S. Pat. No. 7,368,486 discloses dental compositions for making artificial teeth and/or their enamel or cutting area. The dental composition comprises MMA, crosslinked PMMA, splinter polymer, and a methacrylate-based pearl polymer, in which inorganic dental glass is polymerized as filler, Rosenfeld, U.S. Pat. No. 7,189,076 discloses a method of making an artificial tooth for a denture and the tooth so made, the method including making a form tooth of a plastic tooth or an existing denture tooth, using the form tooth to make a mold form, placing a thin layer of polycarbonate incisal material in the bottom of the mold form and conforming the material to the mold form, subjecting the layer of incisal and body material to a vacuum and then to a curing light in an oxygen-free atmosphere, adding additional layers of approximately 2 mm of the incisal and body material and exposing each layer to a vacuum and light curing step until the mold form is full. The tooth is then removed from the mold form and again exposed to a vacuum and light curing step.

Liu, U.S. Pat. No. 6,384,107 discloses dental compositions, products, and processes using silicon containing abrasion resistant material. The produced dental products are abrasion-resistant and self-lubricating across their entire cross sections. Dental compositions useful for forming dental products in accordance with the invention preferably include an ethylenically unsaturated silane. The composition is formed into a dental prosthesis such as an artificial tooth, inlay, onlay, facing, crown or bridge.

Oswald et al., EP 1,264,581 discloses a synthetic material tooth which is built up from a photopolymerizable incisor material, a photopolymerizable dentin material and, optionally, at least one other photopolymerizable material in successive intensively bonded together layers, characterized in that injection-molded or cast nipples are provided at the boundary surfaces of the layers.

Deguchi et al., U.S. Pat. No. 6,063,830 provides a dental curable composition wherein an inorganic filler treated with a silane compound is uniformly dispersed in a fine state in urethane (meth)acrylate, thereby imparting strong toughness, wear resistance, transparency and moldability to an artificial tooth. The colloidal silica has an average primary particle size of from 1 to 85 nm, with at least one silane specific compound.

Nagel et al., EP 0,677,286 discloses artificial teeth containing polymethacrylate, barium aluminium silicate glass and microfine silica, characterized in that it essentially consists of 15-35% by weight of polymethacrylate, 35-75% by weight of barium aluminium silicate glass having a mean particle size of 0.1-5 micrometers, and 5-25% by weight of silica having a mean particle size of 0.01-0.2 micrometer.

Tateosian et al., U.S. Pat. No. 4,698,373 discloses compositions that are hardenable by exposure to heat or electromagnetic radiation by dissolving them together to form a blend form about 0% to about 50% by weight of an uncross-linked polymer, from about 2% to about 30% of a polymerizable monomer, from about 10% to about 70% of a cross-linked polymer in the form of discrete particles having average diameters of from 0.001 micron to about 500 microns and being swollen in said solution and from about 20% to about 70% of a crosslinking agent for said monomer.

Roemer et al., U.S. Pat. Nos. 4,396,476 and 4,396,377 disclose compositions hardenable by exposure to heat or electromagnetic radiation by blending form about 0% to about 50% by weight of an uncross-linked polymer, from about 20% to about 66% of a polymerizable monomer capable of dissolving said polymer, from about 10% to about 70% of a cross-linked polymer in the form of discrete particles having average diameters of from 0.001 micron to about 500 microns and being swollen in said monomer, and from about 0.25% to about 27% of a cross-linking agent for said monomer.

Although some artificial teeth materials described in the patent literature have some desirable properties, there is a need for developing new tooth materials with improved wear resistance and esthetics that are easy to manufacture. In general, artificial teeth made from the combination of composite and acrylic compositions are not easy to manufacture and the use of inorganic fillers in composite can potentially abrade the tooth molds. Artificial teeth made of currently available acrylic compositions incorporating cross-linked polymers and cross-linking agents tend to not provide sufficient wear resistance.

One object of this invention is to provide compositions which are useful in the construction of artificial teeth and their enamel layers along with other dental appliances. The compositions of this invention lead to products having improved wear resistance and superior physical and esthetic characteristics.

SUMMARY OF INVENTION

In general, the novel compositions of this invention are useful in the formation and construction of artificial teeth, their ename layers, veneers, crowns and bridges, dentures, dental appliances, prosthetics, and the like.

In accordance with a preferred version of the present invention, polymerizable dental compositions are provided which may easily and conveniently be molded by known techniques into prosthetic appliances. The resulting appliances possess chemical and physical properties which are significantly improved over those of conventional prior art acrylic dental appliances. Notably, dental appliances, such as, for example, prosthetic teeth produced from precursor blend compositions of this invention are characterized by improved wear resistance which is up to five times greater than the wear resistance of premium plastic teeth commercially marketed at this time.

Furthermore, prosthetic teeth produced from compositions of the invention have excellent stain, chemical and solvent resistances. They also have excellent bonding strength to acrylic denture bases, which is superior to some premium plastic teeth in the market.

In comparison with conventional Interpenetrating polymer Network (IPN) and acrylic teeth, the prosthetic teeth especially enamel surfaces produced in accordance with the invention are characterized by outstanding wear resistance, excellent monomer and solvent resistance, outstanding thermal stability, improved hardness, density, and stain resistance and excellent hydrolytic stability. Teeth produced from the compositions of the invention exhibit excellent gloss when molded. During denture fabrication, the surface gloss of these teeth is maintained over longer periods than conventional acrylic plastic teeth due to their superior chemical and wear resistances.

The prosthetic teeth, especially enamel surfaces, thus formed may be further characterized as having a multiple phase microstructure, where a first extremely hard and wear resistant phase is from highly cross-linked polymer particles, and a second rest hard and highly wear resistance phase is made of cross-linked and interpenetrating polymer network (IPN). The superior physical characteristics, especially wear resistance, of the articles of the invention are believed to be due, at least in part, to this microstructure.

The precursor blend is formed in accordance with the invention by combining a monomer, crosslinking agents for said monomer, a highly cross-linked ground polymer particles with superior hardness and wear resistance, cross-linked polymer and an optional uncross-linked polymer, and/or an initiator and by allowing said combination to age or mature.

In general, the cross-linked polymers which are useful in the practice of the invention are formed from monomers or blends of monomers together with cross-linking agents in proper proportion. Monomer compounds that can be used in the composition of this invention, include, but are not limited to, methyl methacrylate, methyl acrylate, ethyl methacrylate, isobutyl methacrylate, cyclohexylmethacrylate, isobornyl methacrylate, isobornyl acrylate, allyl methacrylate, etc.

Cross-linking agents that can be used in the composition of this invention, include, but are not limited to, di- or polyacrylates and methacrylates such as glycerol di(meth)acrylate, glycerol tri(meth)acrylate, ethyleneglycol di(meth)acrylate, diethyleneglycol di(meth)acrylate, triethyleneglycol dimethacrylate, tetraethylene glycol di(meth)acrylate, 1,3-propanediol di(meth)acrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol tri(meth)acrylate, pentaerythritol tetra(meth)acrylate, pentaerythritol tetramethacrylate, sorbitol hexacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers, etc.

The highly cross-linked polymer is in the form of ground particles having average diameters ranging from about 0.01 micron to about 1,000 microns. Preferably, particles have diameters ranging from 0.05 micron to about 500 microns are used. More preferably, particles have diameters ranging from 0.1 micron to about 200 microns are used. The highly cross-linked polymer particles are fully dispersed into the monomer, cross-linking agents, and remaining polymers. The surfaces of the cross-linked polymer particles can only be slightly softened and penetrated by the monomer so as to maintain a distinct hard phase in the composition and provide adequate bonding to the rest of components in the composition. This becomes part of the cross-linked and interpenetrating polymer network. It has been discovered that the composition of this highly cross-linked polymer and relative proportion of this polymer dramatically affect the wear resistance of final cured composition as well as the handling properties at uncured stage. This invention provides components for a composition having many desired properties. The final hardened or cured product produced from these compositions also have many desirable properties, notably wear resistance.

The cross-linked polymer is in the form of discreet particles having average diameters ranging from about 0.001 micron to about 500 microns. Preferably, at least 50% by weight of said particles have diameters less than 150 microns, and more preferably, less than 100 microns.

It has been discovered that the relative proportions of the components of the precursor blend are critical to obtaining the desired handling properties at uncured stage. It has been discovered that the relative proportions of the components of the precursor blend are critical to obtaining the desired properties in the final hardened or cured product produced, notably the wear resistance, bond strength, flexural properties, impact strength, fracture toughness, resistance to MMA monomer and other solvents, stain resistance, thermal stability, and hydrolytic stability. Thus, it has been discovered that blends of from about 0 to 50, preferably from about 5 to 40, and most preferably from about 5 to 35 weight percent of the cross-linked polymer, from 0 to 50, preferably from about 0 to 40, and most preferably from about 5 to 35 weight percent of uncross-linked polymer, from about 0 to 40, preferably from 10 to 40, and most preferably from about 5 to 35 weight percent of highly cross-linked polymer particles, from about 0 to 50, preferably from about 2 to about 45, and most preferably from about 20 to 35 weight percent of polymerizable monomer, and from about 5 to about 40, preferably from about 5 to 35, and most preferably from about 10 to 30 weight percent of cross-linked agents for said monomer, together with minor amounts of initiator and in some cases activator for the initiator, provide blends which are particularly useful in the production of prosthetic teeth or enamel layers of prosthetic teeth. The resulting articles have desirable properties, particularly wear resistance that is far superior to those of conventional acrylic systems now used in the art. One key feature of this system is the introduction of unique highly cross-linked polymer particles, which is made with desired components and cross-linking density. This materials surprisingly enhance the wear resistance of cured product surprisingly.

The highly cross-linked polymer particles are insoluble and can maintain their shapes in the cured product. The particles will not imbibe the liquid polymerizable monomer but the surface of particles is slightly swellable in the liquid polymerizable monomer component used in preparation of the precursor blend. The highly cross-linked polymer, itself, has high wear resistance. Surprisingly, adding about 10 to about 40 weight percent of the highly cross-linked polymer particles increased the wear resistance of the cured product significantly. In contrast, when about 10 to about 50 weight percent of inorganic particles (non cross-linked particles) were used, they were unable to increase the wear resistance of cured product to the same level. This is somewhat surprising, since the inorganic particles have much higher wear resistance, by themselves, than that of highly cross-linked polymer particles. Using highly cross-linked polymers enhances the wear resistance of the prosthetic teeth or enamel layers of the prosthetic teeth.

The highly crosslinked polymer comprises a polymerized mixture of two or more monomers, oligomers, or polymers, which are selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis[4-(2-hydroxy-3-acryloyloxypropoxy)phenyl]propane; 2,2-bis[4-(2-hydroxy-3-methacryloyloxypropoxy)phenyl] propane (Bis-GMA); 2,2-bis[4-(acryloyloxy-ethoxy) phenylpropane; 2,2-bis[4-(methacryloyloxy-ethoxy)phenyl] propane (or ethoxylated bisphenol A-dimethacrylate) (EBPADMA); urethane di(meth)acrylate (UDMA), diurethane dimethacrylate (DUDMA), 4,13-dioxo-3,14 dioxa-5, 12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

One advantageous property of the cross-linked polymer particles is that they are insoluble in (but will absorb or imbibe) the liquid polymerizable monomer component used in the preparation of the precursor blend. Uncross-linked polymer particles, if used, may be characterized as being capable of dissolving in or being dispersed by the liquid polymerizable monomer.

Many prior art materials used inorganic particles or fillers to enhance the wear resistance of enamel layers of prosthetic teeth or prosthetic teeth with limited success. One problem with using such inorganic particles was that they tended to abrade the mold forms used to mold the prosthetic teeth. This invention used a novel approach by incorporating highly cross-linked polymer particles to enhance the wear resistance of the compositions. The compositions of this invention do not contain inorganic fillers as found in conventional materials. Moreover, the compositions will not damage the mold forms used to make the prosthetic teeth.

It is appreciated that the composition of the present invention may further comprise one or more members selected from the group consisting of free radical initiators, photochemical initiators, activators, pigments, fillers, adhesion modifiers and radiopaquing agents.

The present invention is further illustrated by the following examples, but these examples should not be construed as limiting the scope of the invention.

EXAMPLES

Example 1

A highly crosslinked polymer powder was prepared from the following composition:

| | |
|---|---|
| 25.0% | methyl methacrylate |
| 15.5% | 2,2-bis(4-methacryloxyphenyl)propane |

-continued

| | |
|---|---|
| 14.0% | 1,6-hexanediol dimthacrylate |
| 45.0% | 1,4-cyclohexanediol dimethacrylate |
| 0.5% | benzoyl peroxide |
| 100.0% | |

Above composition was prepared by dissolution and melting to form a homogeneous mixture and subsequently polymerized and ground to polymer powder with average diameters ranging from about 0.001 micron to about 500 microns.

Example 2

A precursor blend for prosthetic teeth was prepared from the following composition:

| | |
|---|---|
| 30.0% | polymer powder of Example 1 |
| 13.35% | poly(methyl methacrylate-co-ethylene dimethacrylate) (99.2:0.8) |
| 6.65% | poly(methyl methacrylate) |
| 25.0% | methyl methacrylate |
| 7.5% | 2,2-bis(4-methacryloxyphenyl)propane |
| 5.0% | A reaction product of trimethyl 1,6-diisocyanatohexane and bisphenol A propoxylate and 2-hydroxyethyl methacrylate |
| 12.25% | 1,4-cyclohexanediol dimethacrylate |
| 0.25% | benzoyl peroxide |
| 100.0% | |

The benzoyl peroxide, 2,2-bis(4-methacryloxyphenyl)propane, the reaction product of trimethyl 1,6-diisocyanatohexane and bisphenol A propoxylate and 2-hydroxyethyl methacrylate, and 1,4-cyclohexanediol dimethacrylate were dissolved in the methyl methacrylate at ambient temperature to form a monomer solution, then mixed with polymer powder of Example 1 and poly(methyl methacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 3

A highly crosslinked polymer powder was prepared from the following composition:

| | |
|---|---|
| 23.36% | poly(methyl methacrylate-co-ethylene dimethacrylate) (99.2:0.8) |
| 11.64% | poly(methyl methacrylate) |
| 20.0% | 1,6-hexanediol dimthacrylate |
| 44.5% | 1,4-cyclohexanediol dimethacrylate |
| 0.5% | benzoyl peroxide |
| 100.0% | |

Above composition was prepared by melting to form a dough mixture and subsequently polymerized and ground to polymer powder with average diameters ranging from about 0.001 micron to about 500 microns.

Example 4

A precursor blend for prosthetic teeth was prepared from the following composition:

| | |
|---|---|
| 25.0% | polymer powder of Example 3 |
| 16.69% | poly(methyl methacrylate-co-ethylene dimethacrylate) (99.2:0.8) |
| 8.31% | poly(methyl methacrylate) |
| 41.25% | methyl methacrylate |
| 8.5% | 2,2-bis(4-methacryloxyphenyl)propane |
| 0.25% | benzoyl peroxide |
| 100.0% | |

The benzoyl peroxide, and 2,2-bis(4-methacryloxyphenyl)propane were dissolved in the methyl methacrylate at ambient temperature to form a monomer solution, then mixed with polymer powder of Example 3, poly(methyl methacrylate) and poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have good wear resistance, which is improved over samples without the use of polymer powder of Example 3.

Example 5

A highly crosslinked polymer powder was prepared from the following composition:

| | |
|---|---|
| 20.0% | methyl methacrylate |
| 17.5% | 2,2-bis(4-methacryloxyphenyl)propane |
| 62.0% | 1,4-cyclohexanediol dimethacrylate |
| 0.5% | benzoyl peroxide |
| 100.0% | |

Above composition was prepared by dissolution and melting to form a mixture and subsequently polymerized and ground to polymer powder with average diameters ranging from about 0.001 micron to about 500 microns.

Example 6

A precursor blend for the enamel of prosthetic teeth was prepared from the following composition:

| | |
|---|---|
| 50.0% | polymer powder of Example 5 |
| 30.0% | A reaction product of trimethyl 1,6-diisocyanatohexane and bisphenol A propoxylate and 2-hydroxyethyl methacrylate |
| 8.0% | 2,2-bis(4-methacryloxyphenyl)propane |
| 1.75% | methyl methacrylate |
| 10.0% | 1,4-cyclohexanediol dimethacrylate |
| 0.25% | benzoyl peroxide |
| 100.0% | |

One part of benzoyl peroxide was dissolved in 7 parts of methyl methacrylate at ambient temperature to form an initiator solution, then mixed with polymer powder of Example 5, and other monomers and oligomer to form a precursor blend mixture (dough-like consistence). The enamel layers of prosthetic teeth were molded from the resultant precursor blend mixture. The resulting teeth have excellent wear resistance.

Example 7

A precursor blend for prosthetic teeth was prepared from the following composition:

| | |
|---|---|
| 24.5% | polymer powder of Example 5 |
| 13.68% | poly(methyl methacrylate-co-ethylene dimethacrylate) (99.2:0.8) |
| 6.82% | poly(methyl methacrylate) |
| 27.5% | methyl methacrylate |
| 8.25% | 2,2-bis(4-methacryloxyphenyl)propane |
| 5.5% | A reaction product of trimethyl 1,6-diisocyanatohexane and bisphenol A propoxylate and 2-hydroxyethyl methacrylate |
| 13.48% | 1,4-cyclohexanediol dimethacrylate |
| 0.27% | benzoyl peroxide |
| 100.0% | |

The benzoyl peroxide, 2,2-bis(4-methacryloxyphenyl)propane, the reaction product of trimethyl 1,6-diisocyanatohexane and bisphenol A propoxylate and 2-hydroxyethyl methacrylate, and 1,4-cyclohexanediol dimethacrylate were dissolved in the methyl methacrylate at ambient temperature to form a monomer solution, then mixed with polymer powder of Example 7 and poly(methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 8

A highly crosslinked polymer powder was prepared from the following composition:

| | |
|---|---|
| 20.0% | methyl methacrylate |
| 25.0% | A reaction product of trimethyl 1,6-diisocyanatohexane and bisphenol A propoxylate and 2-hydroxyethyl methacrylate |
| 54.5% | 1,4-cyclohexanediol dimethacrylate |
| 0.5% | benzoyl peroxide |
| 100.0% | |

Above composition was prepared by dissolution and melting to form a homogeneous mixture and subsequently polymerized and ground to polymer powder with average diameters ranging from about 0.001 micron to about 500 microns.

Example 9

A precursor blend for prosthetic teeth was prepared from the following composition:

| | |
|---|---|
| 24.5% | polymer powder of Example 8 |
| 19.69% | poly(methyl methacrylate-co-ethylene dimethacrylate) (99.2:0.8) |
| 9.81% | poly(methyl methacrylate) |
| 26.68% | methyl methacrylate |
| 7.13% | 1,4-cyclohexanediol dimethacrylate |
| 7.36% | 2,2-bis(4-methacryloxyphenyl)propane |
| 4.60% | ethylene glycol dimethacrylate |
| 0.23% | benzoyl peroxide |
| 100.0% | |

The benzoyl peroxide, 2,2-bis(4-methacryloxyphenyl)propane, ethylene glycol dimethacrylate, and 1,4-cyclohexanediol dimethacrylate were dissolved in the methyl methacrylate at ambient temperature to form a monomer solution, then mixed with polymer powder of Example 8 and poly(methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 10

A highly crosslinked flexible polymer powder was prepared from the following composition:

| | |
|---|---|
| 57.2% | A reaction product of trimethyl 1,6-diisocyanatohexane and bisphenol A propoxylate and 2-hydroxyethyl methacrylate |
| 17.3% | G4246 |
| 17.3% | Cap-SMA |
| 2.3% | Octadecyl acrylate |
| 5.2% | Ethoxylated bisphenol A dimethacrylate |
| 0.35% | Initiator's mixture (containing 0.047% Camphorquinone) |
| 0.35% | 2,4,6 Trimethylbenzoyldiphenylphosphine oxide (Lucirin-TPO) |
| 100.0% | |

Above composition was prepared by melting to form a homogeneous mixture and subsequently polymerized and ground to polymer powder with average diameters ranging from about 0.001 micron to about 500 microns.

Example 11

A highly crosslinked polymer powder was prepared from the following composition:

| | |
|---|---|
| 20.0% | Methyl methacrylate |
| 5.0% | Polymer powder of Example 10 |
| 17.5% | 2,2-bis(4-methacryloxyphenyl)propane |
| 57.0% | 1,4-cyclohexanediol dimethacrylate |
| 0.5% | Benzoyl peroxide |
| 100.0% | |

Above composition was prepared by mixing to form a mixture and subsequently polymerized and ground to polymer powder with average diameters ranging from about 0.001 micron to about 500 microns.

Example 12

A precursor blend for prosthetic teeth was prepared from the following composition:

| | |
|---|---|
| 25.0% | polymer powder of Example 11 |
| 16.35% | poly(methyl methacrylate-co-ethylene dimethacrylate) (99.2:0.8) |
| 8.15% | poly(methyl methacrylate) |
| 24.0% | methyl methacrylate |
| 8.0% | 2,2-bis(4-methacryloxyphenyl)propane |
| 5.0% | 1,4-cyclohexanediol dimethacrylate |
| 12.75% | ethylene glycol dimethacrylate |
| 0.25% | benzoyl peroxide |
| 100.0% | |

The benzoyl peroxide, 2,2-bis(4-methacryloxyphenyl)propane, the reaction product of trimethyl 1,6-diisocyanatohexane and bisphenol A propoxylate and 2-hydroxyethyl methacrylate, and 1,4-cyclohexanediol dimethacrylate were dissolved in the methyl methacrylate at ambient temperature to form a monomer solution, then mixed with polymer powder of Example 11 and poly(methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 13

A precursor blend for prosthetic teeth was prepared from the following composition:

| | |
|---|---|
| 32.70% | poly(methyl methacrylate-co-ethylene dimethacrylate) (99.2:0.8) |
| 16.30% | poly(methyl methacrylate) |
| 29.55% | methyl methacrylate |
| 8.2% | 2,2-bis(4-methacryloxyphenyl)propane |
| 7.9% | 1,4-cyclohexanediol dimethacrylate |
| 5.1% | ethylene glycol dimethacrylate |
| 0.25% | benzoyl peroxide |
| 100.0% | |

The benzoyl peroxide, 2,2-bis(4-methacryloxyphenyl)propane, ethylene glycol dimethacrylate, and 1,4-cyclohexanediol dimethacrylate were dissolved in the methyl methacrylate at ambient temperature to form a monomer solution, then mixed with polymer powder of Example 13 and poly(methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 14

A precursor blend for prosthetic teeth was prepared from the following composition:

| | |
|---|---|
| 36.04% | poly(methyl methacrylate-co-ethylene dimethacrylate) (99.2:0.8) |
| 17.96% | poly(methyl methacrylate) |
| 26.67% | methyl methacrylate |
| 7.4% | 2,2-bis(4-methacryloxyphenyl)propane |
| 7.1% | 1,4-cyclohexanediol dimethacrylate |
| 4.6% | ethylene glycol dimethacrylate |
| 0.23% | benzoyl peroxide |
| 100.0% | |

The benzoyl peroxide, 2,2-bis(4-methacryloxyphenyl)propane, ethylene glycol dimethacrylate, and 1,4-cyclohexanediol dimethacrylate were dissolved in the methyl methacrylate at ambient temperature to form a monomer solution, then mixed with polymer powder of Example 13 and poly(methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 15

A highly crosslinked polymer powder was prepared from the following composition:

| | |
|---|---|
| 20.0% | methyl methacrylate |
| 9.5% | 2,2-bis(4-methacryloxyphenyl)propane |
| 70.0% | 1,4-cyclohexanediol dimethacrylate |
| 0.5% | benzoyl peroxide |
| 100.0% | |

Above composition was prepared by dissolution and melting to form a mixture and subsequently polymerized and ground to polymer powder with average diameters ranging from about 0.001 micron to about 500 microns.

Example 16

A precursor blend for prosthetic teeth was prepared from the following composition:

| | |
|---|---|
| 24.5% | polymer powder of Example 15 |
| 16.35% | poly(methyl methacrylate-co-ethylene dimethacrylate) (99.2:0.8) |
| 8.15% | poly(methyl methacrylate) |
| 29.55% | methyl methacrylate |
| 8.2% | 2,2-bis(4-methacryloxyphenyl)propane |
| 7.9% | 1,4-cyclohexanediol dimethacrylate |
| 5.1% | ethylene glycol dimethacrylate |
| 0.25% | benzoyl peroxide |
| 100.0% | |

The benzoyl peroxide, 2,2-bis(4-methacryloxyphenyl)propane, ethylene glycol dimethacrylate, and 1,4-cyclohexanediol dimethacrylate were dissolved in the methyl methacrylate at ambient temperature to form a monomer solution, then mixed with polymer powder of Example 13 and poly(methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Example 17

A precursor blend for prosthetic teeth was prepared from the following composition:

| | |
|---|---|
| 24.5% | polymer powder of Example 15 |
| 13.68% | poly(methyl methacrylate-co-ethylene dimethacrylate) (99.2:0.8) |
| 6.82% | poly(methyl methacrylate) |
| 31.9% | methyl methacrylate |
| 8.8% | 2,2-bis(4-methacryloxyphenyl)propane |
| 8.53% | 1,4-cyclohexanediol dimethacrylate |
| 5.5% | ethylene glycol dimethacrylate |
| 0.27% | benzoyl peroxide |
| 100.0% | |

The benzoyl peroxide, 2,2-bis(4-methacryloxyphenyl) propane, ethylene glycol dimethacrylate, and 1,4-cyclohexanediol dimethacrylate were dissolved in the methyl methacrylate at ambient temperature to form a monomer solution, then mixed with polymer powder of Example 13 and poly (methyl methacrylate), poly(methyl methacrylate-co-ethylene dimethacrylate) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature. The resulting teeth have excellent wear resistance.

Wear Resistance Tests

Wear resistance was tested using a three-body cyclic abrasion wear machine (Leinfelder method) at 37° C. Localized wear was measured by determining volume loss in mm3 after 400,000 cycles at 50 RPM.

Wear loss of tooth materials of this invention vs. commercially available tooth materials tested at 37° C.

| Material | Volume loss (37° C., mm³) | S.D. |
| --- | --- | --- |
| Example 2 | 0.030 | 0.017 |
| Example 4 | 0.060 | 0.005 |
| Example 6 | 0.017 | 0.003 |
| Example 7 | 0.023 | 0.009 |
| Example 9 | | |
| Example 12 | 0.030 | 0.009 |
| Example 13 | 0.066 | 0.008 |
| Example 14 | 0.053 | 0.006 |
| Example 16 | 0.030 | 0.006 |
| Example 17 | 0.020 | 0.010 |
| Kenson Teeth (RT) | 0.075 (RT) | 0.015 |
| Kenson Teeth | 0.167 | 0.008 |
| IPN Teeth (RT) | 0.050 (RT) | 0.004 |
| IPN Teeth | 0.098 | 0.008 |

It should be understand that while the present invention has been described with respect to certain specific embodiments thereof, it should not be considered limited to such embodiments but may be used in other ways without departure from the sprit of the invention and the scope of the appended claims.

What is claimed is:

1. A dental appliance comprising a hard, shaped body having at least one portion comprising a polymerized blend of:
   A) from 0% to about 50% by weight of an uncrosslinked polymer capable of dissolving in component B);
   B) from about 2% to 45% by weight of a monofunctional polymerizable monomer;
   C) from about 10% to 40% by weight of a first crosslinked polymer in the form of ground particles having average diameters up to 500 microns;
   D) from about 5% to 40% by weight of a second crosslinked polymer in the form of discrete particles having average diameters up to 500 microns and being easily swellable by said monomer; and
   E) from about 5% to about 40% by weight of a di- or polyfunctional crosslinking agent;
   wherein said first crosslinked polymer is different from said second crosslinked polymer,
   wherein the first crosslinked polymer particles are not capable of imbibing the monofunctional polymerizable monomer while the second crosslinked polymer particles are capable of imbibing the monofunctional polymerizable monomer.

2. The appliance of claim 1 wherein said second crosslinked polymer is present in an amount of from about 5% to 35% by weight.

3. The appliance of claim 1 wherein said uncrosslinked polymer is present in an amount of from about 5% to 35% by weight.

4. The appliance of claim 1 wherein said polymerizable monomer is present in an amount of from about 20% to 35% by weight.

5. The appliance of claim 1 wherein said crosslinking agent is present in an amount of from about 10% to 30% by weight.

6. The appliance of claim 1, wherein said crosslinking agent is selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis [4-(2-hydroxy-3-acryloyloxypropoxy)phenyl]propane; 2,2-bis[4-(2-hydroxy-3-methacryloyloxypropoxy)phenyl] propane (Bis-GMA); 2,2-bis[4-(acryloyloxy-ethoxy)phenyl] propane; 2,2-bis[4-(methacryloyloxy-ethoxy)phenyl] propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

7. The appliance of claim 1 wherein the composition further comprises one or more members selected from the group consisting of free radical initiators, photochemical initiators, activators, pigments, fillers, adhesion modifiers and radiopaquing agents.

8. The appliance of claim 1 wherein said first crosslinked polymer comprises a polymerized mixture of two or more monomers, oligomers or polymers and one or more cross-linking agents.

9. The appliance of claim 1 wherein said first crosslinked polymer comprises a polymerized mixture of one or more monomers and one or more cross-linking agents selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth) acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis [4-(2-hydroxy-3-acryloyloxypropoxy)phenyl]propane; 2,2-bis[4-(2-hydroxy-3-methacryloyloxypropoxy)phenyl] propane (Bis-GMA); 2,2-bis[4-(acryloyloxy-ethoxy)phenyl]

propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

10. The appliance of claim 5, wherein said crosslinking agent is selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

11. The appliance of claim 1 wherein:
said second crosslinked polymer is present in an amount of from about 5% to 35% by weight;
said uncrosslinked polymer is present in an amount of from about 5% to 35% by weight;
said polymerizable monomer is present in an amount of from about 20% to 35% by weight; and
said crosslinking agent is present in an amount of from about 10% to 30% by weight.

12. The appliance of claim 11 wherein said first crosslinked polymer comprises a polymerized mixture of two or more monomers, or oligomers and one or more cross-linking agents selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

13. The appliance of claim 12 wherein the composition further comprises one or more members selected from the group consisting of free radical initiators, photochemical initiators, activators, pigments, fillers, adhesion modifiers and radiopaquing agents.

14. The appliance of claim 12 wherein the composition further comprises minor amounts of initiator and an activator for the initiator.

15. A dental appliance comprising a hard, shaped body having at least one portion comprising a polymerized blend of:
A) from 0% to about 50% by weight of an uncrosslinked polymer capable of dissolving in component B);
B) from about 2% to 45% by weight of a monofunctional polymerizable monomer;
C) from about 5% to 35% by weight of a first crosslinked polymer in the form of ground particles having average diameters up to 500 microns;
D) from about 5% to 40% by weight of a second crosslinked polymer in the form of discrete particles having average diameters up to 500 microns and being easily swellable by said monomer; and
E) from about 5% to about 40% by weight of a di- or polyfunctional crosslinking agent;
wherein said first crosslinked polymer is different from said second crosslinked polymer,
wherein the first crosslinked polymer particles are not capable of imbibing the monofunctional polymerizable monomer while the second crosslinked polymer particles are capable of imbibing the monofunctional polymerizable monomer.

16. The appliance of claim 15 wherein:
said second crosslinked polymer is present in an amount of from about 5% to 35% by weight;
said uncrosslinked polymer is present in an amount of from about 5% to 35% by weight;
said polymerizable monomer is present in an amount of from about 20% to 35% by weight; and
said crosslinking agent is present in an amount of from about 10% to 30% by weight.

17. The appliance of claim 16, wherein said crosslinking agent is selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

18. The appliance of claim 17 wherein said first crosslinked polymer comprises a polymerized mixture of two or more monomers, or oligomers and one or more cross-linking agents selected from the group consisting of glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexaacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); polyurethane dimethacrylate (PUDMA); alkoxylated pentacrythritol tetraacrylate; polycarbonate dimethacrylate (PCDMA); the bis-acrylates and bis-methacrylates of polyethylene glycols; and copolymerizable mixtures of acrylated monomers and acrylated oligomers.

\* \* \* \* \*